US008900176B2

(12) United States Patent
Bailey (10) Patent No.: US 8,900,176 B2
(45) Date of Patent: Dec. 2, 2014

(54) CHRONIC HEMODIALYSIS CATHETER WITH BALLOON

(75) Inventor: Frances Kristen Bailey, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1020 days.

(21) Appl. No.: 12/971,965

(22) Filed: Dec. 17, 2010

(65) Prior Publication Data

US 2011/0092876 A1 Apr. 21, 2011

Related U.S. Application Data

(62) Division of application No. 11/758,526, filed on Jun. 5, 2007, now abandoned.

(51) Int. Cl.
| | | |
|---|---|---|
| *A61M 37/00* | (2006.01) | |
| *A61M 29/00* | (2006.01) | |
| *A61M 25/10* | (2013.01) | |
| *A61M 25/00* | (2006.01) | |

(52) U.S. Cl.
CPC .......... *A61M 25/10* (2013.01); *A61M 25/0032* (2013.01); *A61M 2025/0031* (2013.01)
USPC .......................... 604/6.16; 606/108; 606/109

(58) Field of Classification Search
CPC ............ A61M 25/0032; A61M 25/10; A61M 2025/0031
USPC .................... 604/4.01–6.16, 101.05, 108, 109
See application file for complete search history.

(56) References Cited

U.S. PATENT DOCUMENTS

| | | | |
|---|---|---|---|
| 3,996,938 A | 12/1976 | Clark, III | |
| RE31,855 E | 3/1985 | Osborne | |
| 4,772,268 A | 9/1988 | Bates | |
| 5,053,023 A | 10/1991 | Martin | |
| 6,056,721 A * | 5/2000 | Shulze | 604/101.05 |
| 6,071,263 A | 6/2000 | Kirkman | |
| 6,261,255 B1 | 7/2001 | Mullis et al. | |
| 6,398,752 B1 | 6/2002 | Sweezer et al. | |
| 6,508,790 B1 | 1/2003 | Lawrence | |

(Continued)

FOREIGN PATENT DOCUMENTS

| | | |
|---|---|---|
| WO | WO 91/10456 A1 | 7/1991 |
| WO | WO 2005/030291 A2 | 4/2005 |

OTHER PUBLICATIONS

"Products for Dialysis;" Cook Interventional Critical Care Products; Cook Incorporated; 2002; 15 pages.

*Primary Examiner* — Philip R Wiest
(74) *Attorney, Agent, or Firm* — Brinks Gilson & Lione (57) ABSTRACT

An indwelling catheter device and a method of treatment using the indwelling catheter device are provided. The indwelling catheter device includes an elongate shaft having a proximal portion, a distal portion, a first lumen extending longitudinally therethrough and an inflation lumen extending at least partially through the shaft. The distal portion of the shaft includes a first opening connected to the first lumen. The catheter device further includes a balloon operably connected to an outer surface of the shaft proximal to the first opening wherein the balloon at least partially surrounds the shaft. The inflation lumen is connected to the balloon for selective inflation and deflation of the balloon for disrupting migration of the occluding material and inhibiting the material from occluding the first opening when the catheter device is indwelling.

20 Claims, 8 Drawing Sheets

(56) References Cited

U.S. PATENT DOCUMENTS

| | | |
|---|---|---|
| 6,692,459 B2 | 2/2004 | Teitelbaum |
| 6,942,635 B2 | 9/2005 | Rosenblatt et al. |
| 7,169,162 B2 | 1/2007 | Garakani |
| 7,678,075 B2 * | 3/2010 | Wantink et al. ............ 604/96.01 |
| 8,246,568 B2 * | 8/2012 | Hardert et al. ............... 604/6.01 |
| 2002/0091362 A1 | 7/2002 | Maginot et al. |
| 2004/0210180 A1 | 10/2004 | Altman |
| 2005/0004504 A1 | 1/2005 | Frye et al. |
| 2005/0055012 A1 | 3/2005 | Trerotola |
| 2005/0065469 A1 * | 3/2005 | Tal ............................ 604/96.01 |
| 2005/0245900 A1 | 11/2005 | Ash |
| 2005/0261663 A1 | 11/2005 | Patterson et al. |
| 2006/0287665 A1 | 12/2006 | Burton et al. |
| 2007/0016124 A1 * | 1/2007 | McGraw ..................... 604/4.01 |

* cited by examiner

CHRONIC HEMODIALYSIS CATHETER WITH BALLOON

This application is a divisional application of U.S. application Ser. No. 11/758,526, filed Jun. 5, 2007, which is incorporated by reference herein in its entirety.

TECHNICAL FIELD

This invention relates generally to indwelling medical devices, and in particular, to catheters susceptible to fibrin deposition, such as catheters for use in hemodialysis treatment.

BACKGROUND OF THE INVENTION

Catheters or other medical devices for placement into a patient's vascular system are used for many procedures. Frequently these devices are left in place for extended periods, especially when the procedures are performed on a periodic basis and can include several treatments per week. For example, some catheters are used in the simultaneous introduction of fluid into the body and withdrawal of fluid from the body. Such indwelling catheters are particularly useful in hemodialysis. The hemodialysis catheter is typically inserted partially within the body with the distal end placed in a blood vessel and the proximal end external to the body and connectable to another device such as a dialysis unit. An indwelling hemodialysis catheter is advantageous in that the patient does not need to have repeated needle insertions into the skin to gain access to the vasculature each time a dialysis procedure is initiated. Any type of indwelling medical device has the advantage of allowing repeated treatments using the same device for access to the body without the need for reinserting the device for each treatment.

However, several disadvantages are associated with leaving an indwelling device in place for an extended period of time. Patients may develop an infection at the insertion site or in the tissue surrounding the indwelling device. In addition, clots or a fibrous sheath may develop and occlude openings in the catheter and provide additional sources for infections to develop. The fibrous sheath originates from the insertion point at the patient's skin and migrates distally along the device until the openings in the device become occluded. The fibrous sheath typically begins to develop within twenty-four hours of insertion of the device into the patient with an initial thrombus present which is composed of platelets, fibrin, red blood cells, and white blood cells. After three days, the thrombi continue to thicken forming a fibrous sheath and within one week, smooth muscle cells infiltrate the fibrous sheath. The surface of the fibrous sheath is covered with endothelial cells oriented in the direction of blood flow. Within two weeks, the sheath is a mixture of smooth muscle cells and collagen and at three to four weeks, the volume of collagen increases and becomes organized in thicker, coiled bundles. After two to six months collagen is the main component. Sufficient migration and development of the fibrous sheath become evident with a decrease in flow rate through the device to indicate that an opening has become at least partially occluded.

Occluding the opening(s) presents the additional problem that successive treatments require substantially more time to adequately perform the procedure and may increase the costs relating to the treatment. The openings may become completely occluded, for example, by the sheath, so that the device must be removed and a new device inserted. Treatments including pharmaceutical compositions have been used during each procedure to try to disrupt the sheath or clot. However, some pharmaceutical compositions may further complicate the treatment and add to the costs of the procedure.

What is needed is an improved medical device and associated methods that disrupt the migration and inhibit the formation of the occluding materials, such as a fibrous sheath, around the device and allow flow to continue through the device at a sufficiently high rate for treatment.

BRIEF SUMMARY OF THE INVENTION

The foregoing problems are solved and a technical advance is achieved in an illustrative medical device having a balloon that is inflatable to disrupt the occlusion of an opening on the indwelling medical device.

In one aspect of the invention, an indwelling catheter device for fluid flow therethrough is provided. The indwelling catheter device includes an elongate shaft having a proximal portion, a distal portion, a first lumen extending longitudinally therethrough and an inflation lumen extending at least partially through the shaft. The distal portion of the shaft includes a first opening connected to the first lumen. The catheter device further includes a balloon operably connected to an outer surface of the shaft proximal to the first opening wherein the balloon at least partially surrounds the shaft. The inflation lumen is connected to the balloon for selective inflation and deflation of the balloon. The balloon is configured for inhibiting occluding material from occluding the first opening when the catheter device is indwelling.

In another aspect of the present invention, a method for intraluminal treatment of a patient employing an indwelling catheter device is provided. The method includes inserting at least a portion of a shaft of a catheter device into a vessel of the patient. The catheter device includes the shaft having a lumen extending longitudinally therethrough having an opening at a distal portion of the shaft and a balloon operably connected to the shaft proximal to the opening. The method further includes providing a treatment through the lumen and inflating the balloon to disrupt a migration of occluding material distally on the shaft so as to inhibit the occluding material from occluding the opening in the distal portion of the shaft. Inflation of the balloon may be before, during or after the treatment or combinations thereof.

In another aspect of the present invention, a method for intraluminal treatment of a patient employing an indwelling catheter device is provided. The method includes inserting a distal end of a shaft of a catheter device into a vessel of the patient. The catheter device includes the shaft having a first lumen extending longitudinally therethrough to a first opening and a second lumen extending longitudinally therethrough to a second opening and a balloon operably connected to the shaft proximal to the first and second openings. The method further includes withdrawing a bodily fluid to be treated from the vessel through the second lumen and treating the fluid in a treatment instrument. The method includes infusing the treated fluid through the first lumen into the vessel and selectively inflating the balloon to inhibit occluding material from occluding the first and second openings.

Advantages of the present invention will become more apparent to those skilled in the art from the following description of the preferred embodiments of the invention which have been shown and described by way of illustration. As will be realized, the invention is capable of other and different embodiments, and its details are capable of modification in

DETAILED DESCRIPTION OF THE INVENTION

Figure 1A:
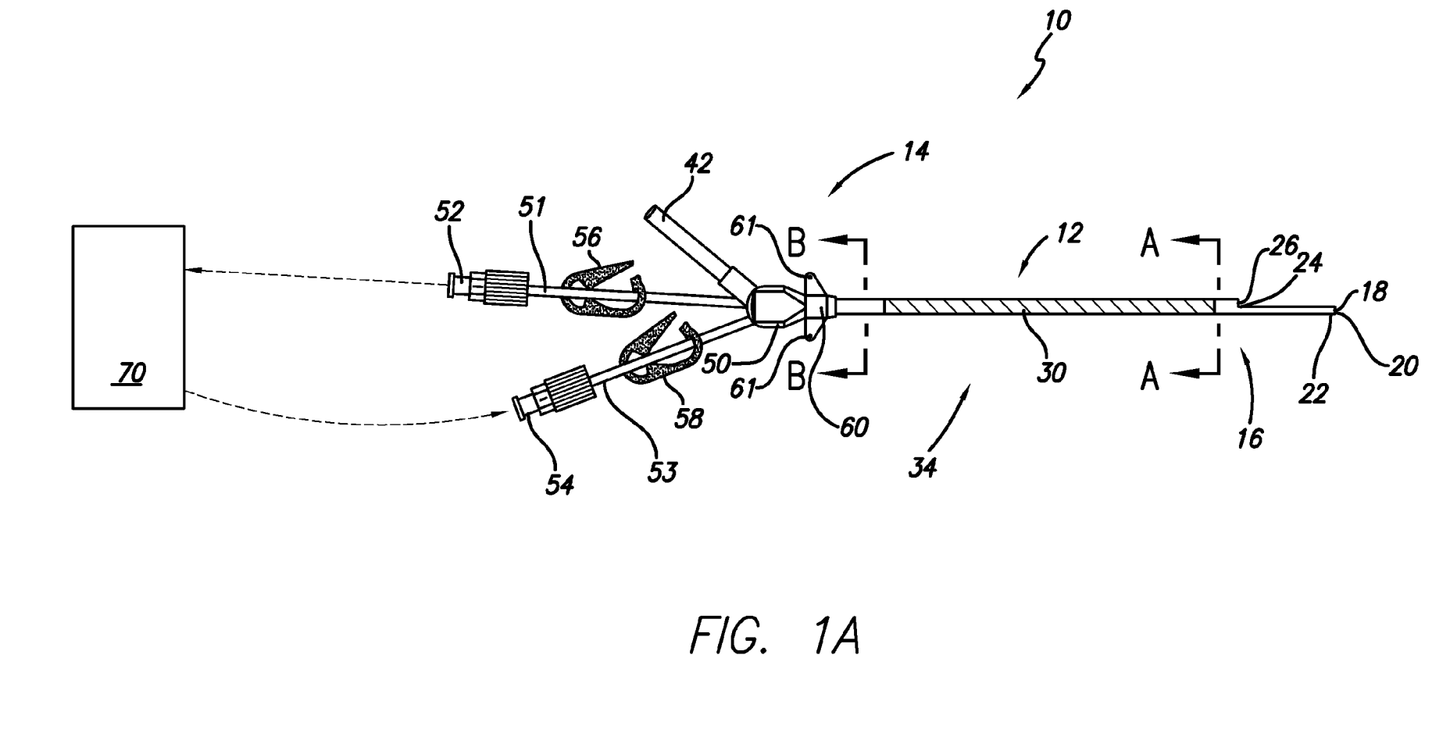
FIG. 1A is a side elevational view of one embodiment of a catheter device of the present invention.
Figure 1B:
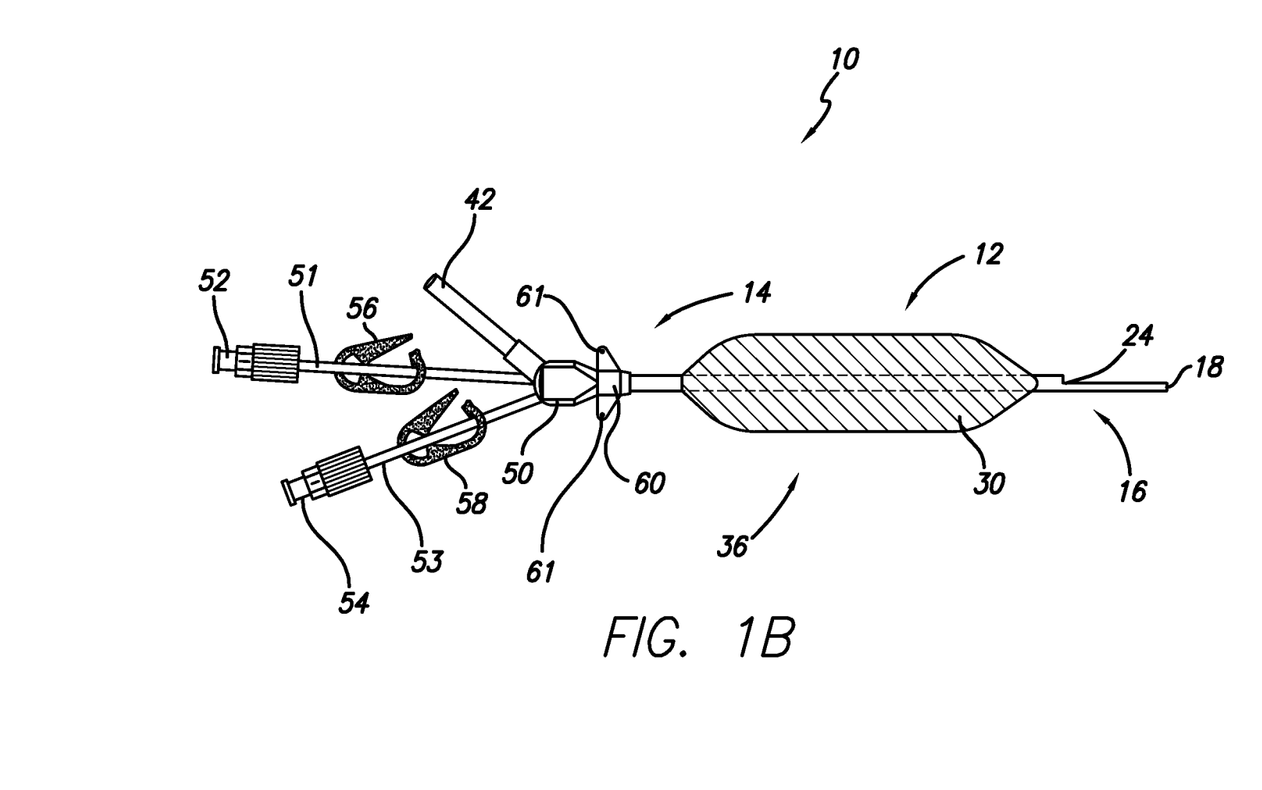
FIG. 1B is a side elevational view of the embodiment shown in FIG. 1A with an inflated balloon.

Several possible embodiments of an indwelling device of the present invention are shown in the figures. The indwelling device of the present invention may be any kind of medical device used for delivering multiple treatments through the indwelling device rather than a single insertion device that is subsequently removed after the single treatment. Indwelling devices of the present invention include, but are not limited to, devices for treatment of the vasculature, urogenital system, and the gastrointestinal tract. FIGS. 1A and 1B illustrate the present invention with reference to a hemodialysis catheter, however the description is intended to be illustrative of the present invention and not limited to such devices. The terms "proximal" and "distal" as used herein to describe the portions of the catheter. The term "proximal portion" refers the portion of the device that is closest to the operator during use of the medical device. The term "distal portion" refers to the portion of the device that is inserted into the patient, or that is closest to the patient.

An indwelling catheter device 10 of the present invention is shown in FIG. 1A. The catheter 10 includes an elongate shaft 12 having a proximal portion 14, a distal portion 16 and a lumen 18 extending through the shaft 12, the lumen 18 having an opening 20 at a distal end 22 of the shaft 12. The catheter 10 shown in FIG. 1A includes a second lumen 24 extending longitudinally through the shaft 12 and having an opening 26 in the distal portion 16. (Lumens 18, 24 shown in FIGS. 2 and 3.) The catheter 10 further includes a balloon 30 operably connected to the shaft 12. As shown in FIGS. 1A and 1B, the balloon 30 extends longitudinally along the shaft 12 from the proximal portion 14 to the distal portion 16. An inflation lumen 32 extends longitudinally along a portion of the shaft 12 and connects to the balloon 30 for selective inflation and deflation of the balloon 30. The inflation lumen 32 is shown in the cross-sectional view of FIG. 3 and shown operably connected to the balloon 30 in FIG. 5. The balloon 30, shown in FIG. 1A, is in a deflated configuration 34 for insertion into the patient and for storage between selective inflations. The balloon 30 may be sized and shaped to narrowly fit against the shaft 12 in the deflated configuration 34.

The balloon 30 is shown in an inflated configuration 36 in FIG. 1B. As will be discussed in more detail below, the balloon 30 may be selectively inflated and deflated after the catheter 10 has been placed in the patient. The balloon 30 may be any type of balloon known in the art and is shaped and dimensioned in the inflated configuration 36 to disrupt the progression of any occluding material that may migrate along the shaft 12 from the proximal portion 14, and eventually to the distal portion 16 if left undisrupted. The inflation lumen 32 may be maintained in connection with the balloon 30 for allowing the balloon to be inflated and deflated using a device such a syringe (not shown) connected to an inflation port 42 that is operably connected to the proximal portion 14 of the shaft 12. The inflation lumen 32 opens into the balloon 30 at a balloon port 44 in the shaft 12 (port 44 shown in FIG. 5). The shape and dimensions of the inflation lumen 32 may be any configuration suitable to permit free flow of inflation medium from the inflation port 42 to the balloon port 44 and back out to the inflation port 42 during inflation and deflation of the balloon 30. The inflation medium may be any liquid (e.g., saline solution) or gas that is suitable for use in patients.

Figure 5:
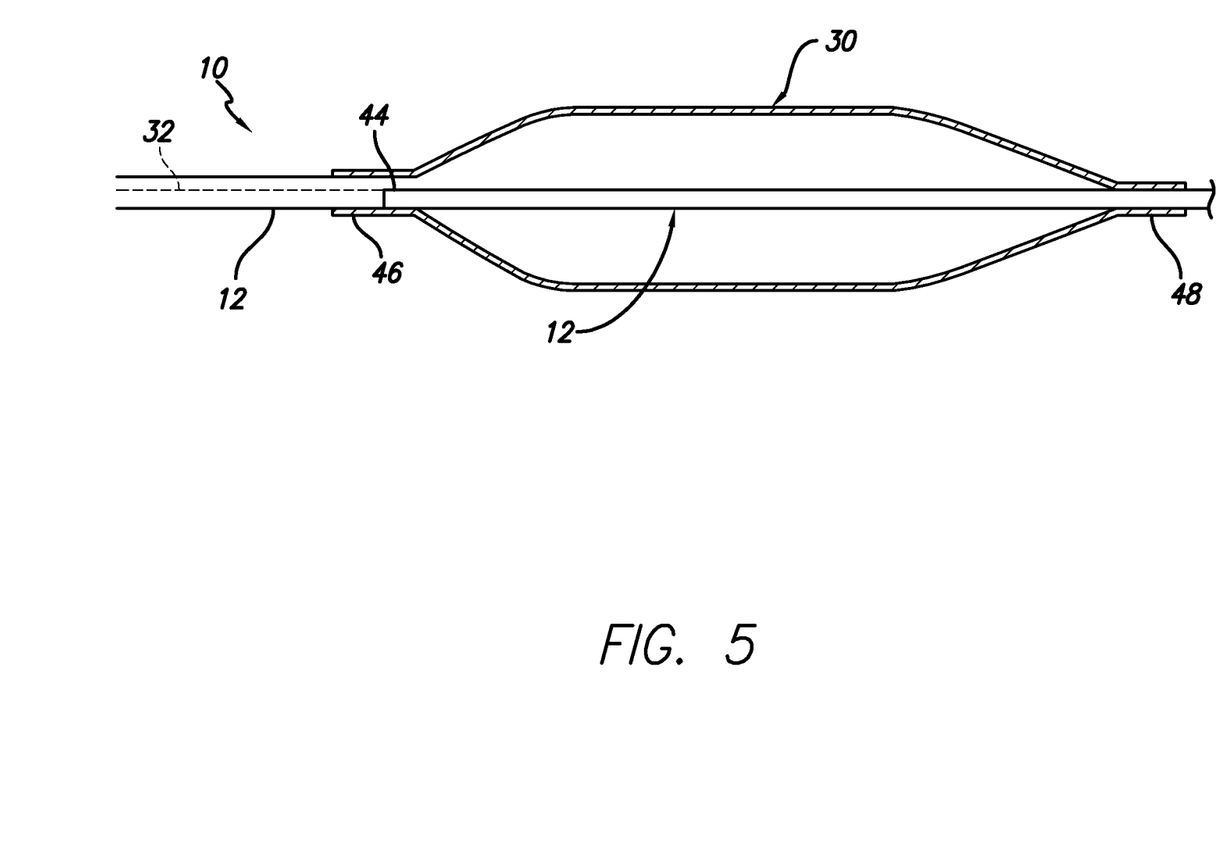
FIG. 5 is an enlarged cross-sectional view of the balloon shown in FIG. 1B.

The balloon 30 may be connected to the shaft 12 by any method known to one skilled in the art wherein the connection allows the balloon 30 to be inflated and deflated through the port 44. For example, the balloon 30 may be bonded to the shaft 12 at a proximal end 46 and a distal end 48 of the balloon 30 as shown in FIG. 5. The balloon 30 may also be attached to the shaft 12 using a clamping band or other device to hold the balloon 30 on the shaft 12 (not shown). The proximal end 46 of the balloon 30 may be connected to the shaft proximally to the balloon port 44 so that inflation medium may freely flow through the port 44 without interference from the connection of the distal end 46 to the shaft 12.

Figure 3:
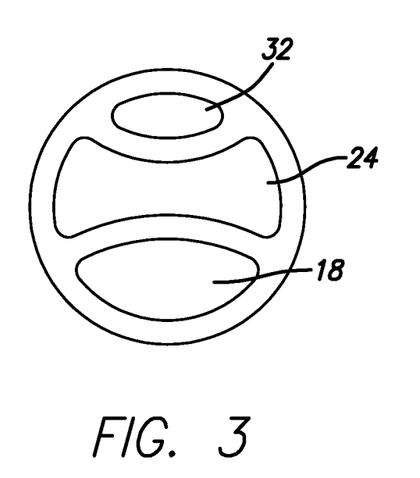
FIG. 3 is an enlarged cross-sectional view taken along the lines B-B of FIG. 1A.
Figure 4:
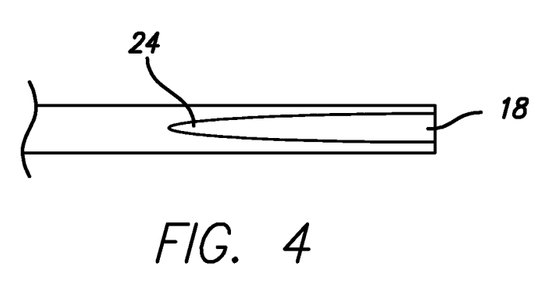
FIG. 4 is a top plan view of the distal end of the catheter device shown in FIG. 1A.

In addition to the inflation lumen 32, the shaft 12 includes the lumens 18 and 24 as shown in FIG. 3. The inflation lumen 32 extends along the shaft 12 to the port 44 as discussed above. The balloon port 44 opens proximal to the openings 20 and 26 of the lumens 18 and 24, respectively. As illustrated in FIG. 1A and in the cross-sectional view in FIG. 3, the lumens 18 and 24 extend distally beyond where the inflation lumen 32 terminates at the port 44 so that the lumens 18 and 24 fluidly connect to the patient at a location distal to the balloon 30. In some embodiments, the opening 26 of the lumen 24 terminates proximal to the opening 20 of the lumen 18 as shown in FIG. 4. The lumen 24 may be configured to withdraw arterial blood through the lumen 24 under negative pressure, into a manifold 50, through tubing 51 and through a connector 52 for further transport and treatment in a manner to be described. The lumen 18 may be configured to infuse or return fluid to the patient. Fluid may be infused into the vessel under positive pressure, from a connector 54, through tubing 53, into the manifold 50 and through the opening 20 of the lumen 18.

Figure 2:
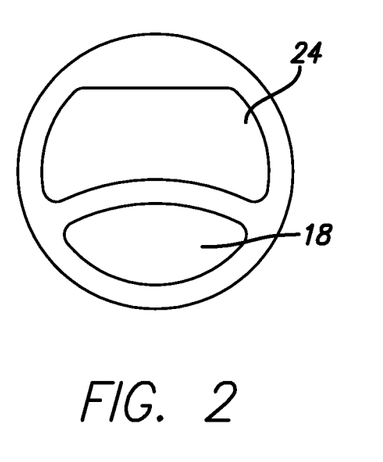
FIG. 2 is an enlarged cross-sectional view taken along the lines A-A of FIG. 1A.

A Luer lock or other suitable connector may engaged with each connector 52, 54 for connecting with a treatment instrument, such as a dialyzer 70, for establishing a flow path of fluid to the dialyzer 70. Clamps 56, 58 maybe provided on the tubing 51, 53, respectively, for selectively opening and closing the tubing 51, 53 for allowing flow between the dialyzer 70 and the catheter 10. Any type of clamping device may be used to control the flow between the dialyzer 70 and the catheter 10. Arrows are provided in FIGS. 1A and 1B to indicate the direction of flow of the treated fluid as it is removed and returned to the patient. Although the lumen 18 and the lumen 24 have been designated in this embodiment as respective infusion and withdrawal lumens, the designations may be reversed if desired. As will be understood by one skilled in the art, the catheter 10 may include any number of lumens, i.e., one, two, three or more. The number of connectors and tubing connected to the manifold will generally correspond to the number of lumens extending through the shaft. As shown in FIGS. 2 and 3, the lumens 18, 24 may be curvilinear in cross-sectional shape and the lumen 24 may be larger than the lumen 18, although the lumens may be any size and shape.

As shown in FIG. 1A, the catheter device 10 may also include a fitting 60 for connecting the shaft 12 and the manifold 50. The fitting 60 may include a pair of projections 61. The projections 61 may be sutured to the skin of the patient to secure the catheter device 10 in position once the catheter device 10 has been inserted into the patient. The fitting 60 may be configured to snap fit together with the manifold 50, although any type of connection may be used to couple the fitting 60 to the manifold 50 and allow fluid to flow through the lumens 18, 24 and inflation media to flow through the lumen 32.

Figure 6A:
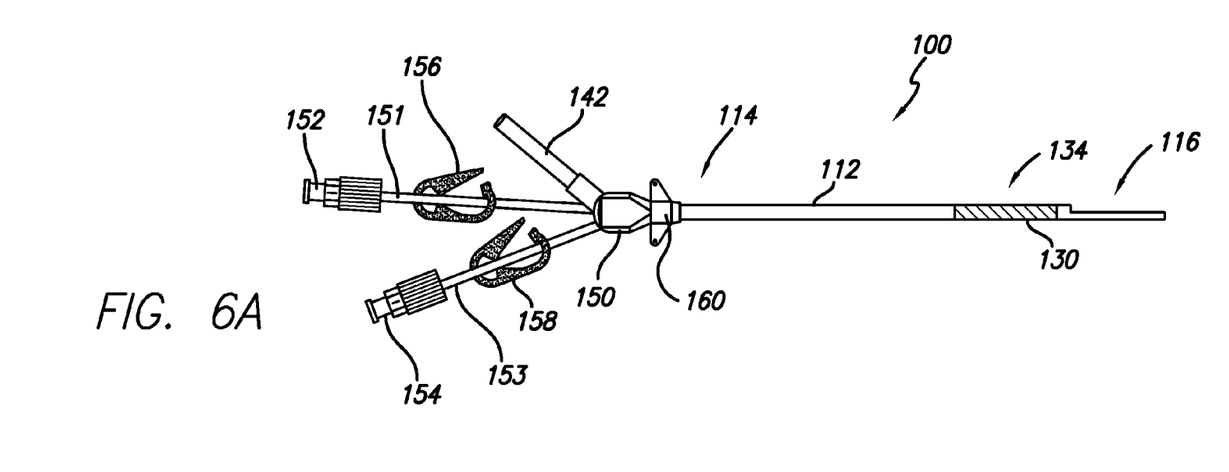
FIG. 6A is a side elevational view of another embodiment of the catheter device of the present invention having a distal balloon.
Figure 6B:
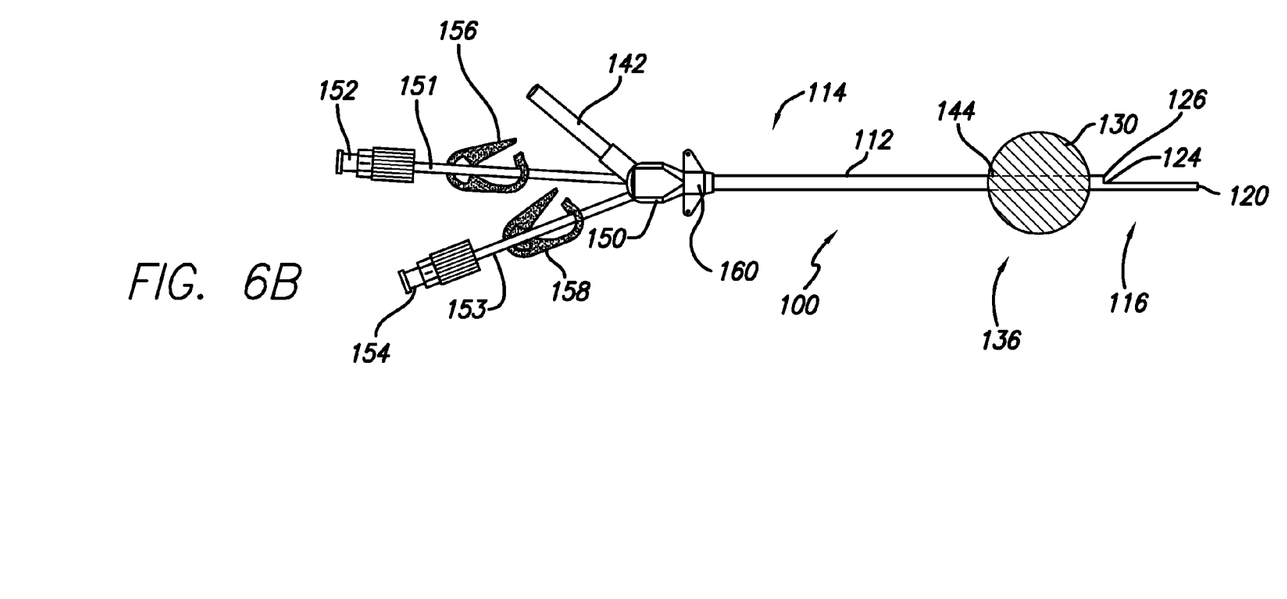
FIG. 6B is a side elevational view of the embodiment shown in FIG. 2A with the balloon inflated.

An alternative embodiment of an indwelling catheter device 100 is shown in FIGS. 6A and 6B. The catheter device 100 is similar to the catheter device 10 described above and differs in the configuration of a balloon 130 attached to a shaft 112. Similar to the catheter device 10, the catheter device 110 includes the shaft 112 having a proximal portion 114 and a distal portion 116. The shaft 112 further includes an opening 120 and an opening 126. Lumens 118 and 124 extend through the shaft 112 similar to the lumens 18 and 24 described above (not shown). The balloon 130 operably connects to the shaft 112 at the distal portion 116 of the shaft 112. An inflation lumen, similar to the lumen 32 above, extends longitudinally along a portion of the shaft 112 and connects to the balloon 130 for selective inflation and deflation of the balloon 130 at a port 144 opening within the balloon 130. The balloon 130, shown in FIG. 6A, is in a deflated configuration 134 for insertion into the patient and for storage between selective inflations. The balloon 130 may be sized and shaped to narrowly fit against the shaft 112 in the deflated configuration 134.

The balloon 130 is shown in an inflated configuration 136 in FIG. 6B. The balloon 130 may be selectively inflated and deflated after the catheter device 100 has been placed in the patient. The balloon 130 may be any type of balloon known in the art and is shaped and dimensioned in the inflated configuration 136 to disrupt the progression of occluding material that may progress along the shaft 112 from the proximal portion 114, and eventually to the distal portion 116 if left undisrupted. Similar to the embodiment described above, the balloon 130 may be inflated and deflated using a syringe and inflating media injected into and withdrawn from an injection port 142. The balloon 130 may be connected to the shaft 112 by any method known to one skilled in the art as discussed above.

Figure 7A:
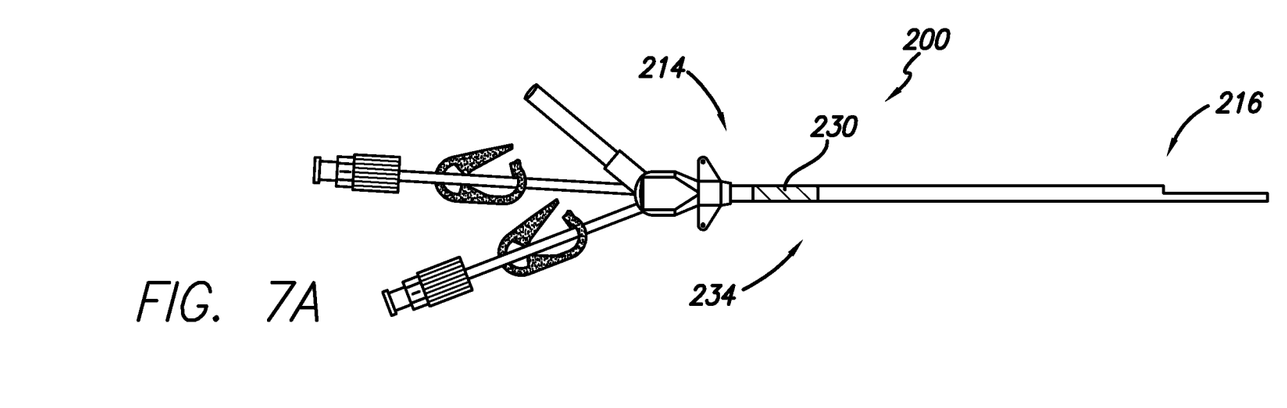
FIG. 7A is a side elevational view of another embodiment of the catheter device of the present invention having a proximal balloon.
Figure 7B:
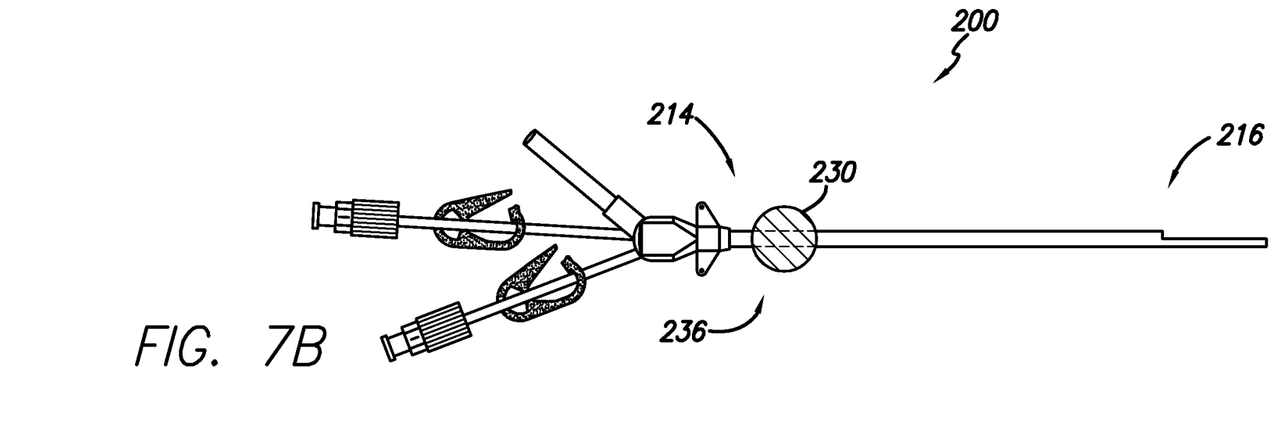
FIG. 7B is a side elevational view of the embodiment shown in FIG. 3A with the balloon inflated.

An alternative embodiment of an indwelling catheter device 200 is shown in FIGS. 7A and 7B. The catheter device 200 is similar to the catheter devices 10, 100 described above and differs in the configuration of a balloon 230 that is attached to a proximal portion 214 of a shaft 212. As shown in FIG. 7A, the balloon 230 is in a deflated configuration 234 and fits narrowly against the shaft 212. FIG. 7B illustrates the balloon 230 in an inflated configuration 236 for disrupting occlusive material as the material progresses distally on the shaft 212. The remaining features of the device 200 are similar to the features described above for the device 10, 100.

Figure 8:
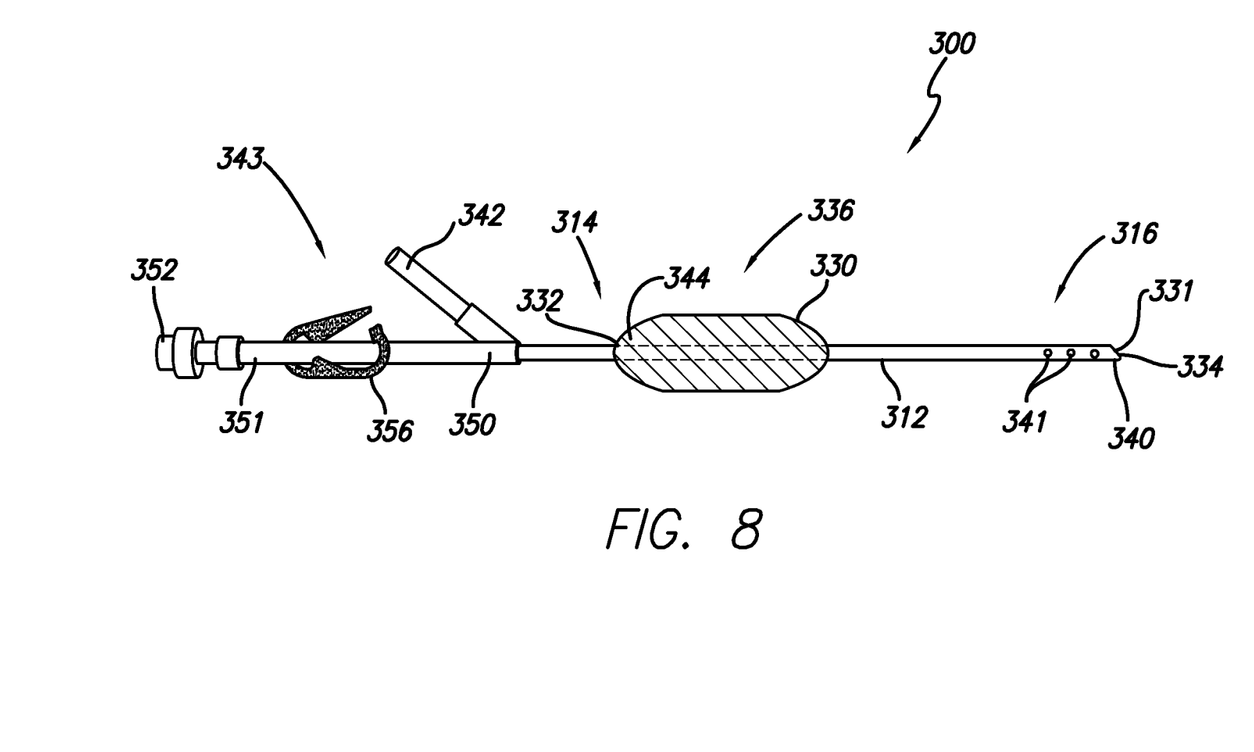
FIG. 8 is side elevational view of another embodiment of the present invention with an inflated balloon.

Another alternative embodiment of an indwelling medical device is shown in FIG. 8. A catheter device 300 includes a shaft 312 having a proximal portion 314, a distal portion 316 and a balloon 330. The shaft 312 includes a lumen 331 extending longitudinally therethrough to an opening 334 at a distal end 340. The shaft 312 may also include a plurality of side ports 341 in the distal portion 316 for fluid flow therethrough. An inflation lumen 332 extends longitudinally along a portion of the shaft 312. The inflation lumen 332 connects to an inflation port 342 at a proximal portion 343 of the catheter 300 and the inflation lumen 332 opens at a balloon port 344 that connects to the balloon 330 for selective inflation and deflation of the balloon 330. The inflation port 342 connects to the inflation lumen 332 in the shaft 312 through a manifold 350. A connector 352 and tubing 351 may also connect to the lumen 331 in the shaft 312 through the manifold 350. The connector 352 may be used for delivery of treatments to the patient. The treatment may be the delivery of medication or connection to a treatment device such as the dialyzer described above. A clamp 356 may be provided for closing the tubing 351 when the patient is not receiving treatment.

The balloon 330 shown in FIG. 8 is in an inflated configuration 336. The balloon may also be in a deflated configuration similar to the deflated configuration described above where the balloon 330 fits narrowly against the shaft 312. The balloon 330 may be similar to the balloons described in the embodiments above. The balloon 330 is shaped and dimensioned in the inflated configuration 336 to disrupt the progression of occluding material that may progress along the shaft 312 from the proximal portion 314, and eventually to the distal portion 316 if left undisrupted.

The balloon for use with the present invention may be any type of inflatable balloon suitable for patient treatment. For example, the balloon may be formed from one or more layers of expandable material, such as polyurethane, radiopaque polyurethane material, thermoplastic polyurethane elastomers, aliphatic polyurethanes, aromatic polyurethanes, styrene-ethylene-butylene-styrene (SEBS) block copolymer, thermoplastic elastomers, low-density polyethylene, polyethylene terephthalate, polyethylene terephthalate glycol, silicone, copolymer of polyurethane and silicone, natural rubber, synthetic rubber, thermoplastic polyamide, nylon, latex, polyethylene, polyisoprene, polyisobutylene, thermoplastic elastomers, an elastomeric material, or combinations thereof.

If desired, various components of the catheter devices and components described herein, such as the shaft, balloon and tubing, can be impregnated or coated with antimicrobial agents to minimize the risk of bacterial colonization of the catheter, and catheter-related bacteremia during use. An example of an antimicrobial combination that has been shown to be an effective antimicrobial composition in percutaneous devices is the combination of antimicrobials minocycline and rifampin. Alternatively, other well-known antimicrobials may be substituted for minocycline and rifampin, which antimicrobials need not necessarily be utilized in combination Operation of the indwelling medical device of the present invention will be described with reference to the catheter device 10 of FIGS. 1A and 1B in a hemodialysis procedure. Initially, the catheter device 10 must be introduced into the vessel of the patient. Suitable percutaneous techniques for insertion of catheter devices into body vessels are well known in the medical arts, and are in widespread use. Perhaps the most widely-utilized technique, and the technique favored herein, is the well-known Seldinger technique. In the Seldinger technique, an injection is made into the vessel interior with a needle, and a wire guide is inserted into the vessel through a bore in the needle. The needle is withdrawn, and an introducer sheath, preferably a splittable sheath, such as a PEEL-AWAY® sheath, available from Cook Incorporated, of Bloomington, Ind., is introduced over the wire guide. The catheter assembly is then introduced into the vessel via the introducer sheath and over the wire guide. The wire guide and the sheath are removed in conventional fashion, leaving at least the distal portion 16 of catheter device 10 in the body vessel.

Once the catheter device 10 has been inserted into a body vessel, sufficient negative pressure is created to commence withdrawal of blood from the vessel, such as by activation of the dialyzer 70. Blood is withdrawn from the vessel through the opening 26 of the lumen 24. The blood is then drawn through lumen 24 in the proximal direction, and passes into the dialyzer 70 by way of a flow path that includes manifold 50, tubing 51 and connector 52. The withdrawn blood is then subjected to treatment in dialyzer 70 in conventional fashion. Following treatment, the cleansed blood is returned to the body vessel by way of a flow path that includes connector 54, tubing 53, manifold 50 and lumen 18. The cleansed blood then re-enters the vessel through opening 20 of the lumen 18.

Once the treatment is completed, the clamps 56, 58 may be closed and the connection between the connectors 52, 54 and the dialyzer 70 disconnected. The treatment process may be repeated several times using the same catheter device 10.

As discussed above, when the indwelling catheter device 10 is placed within the patient, occluding materials tend to begin migrating from the proximal portion 14 of the shaft 12 towards the distal portion 16 of the shaft 12. If the occluding material is not disrupted, the occluding material will eventually occlude the openings 20, 24.

Figure 9A:
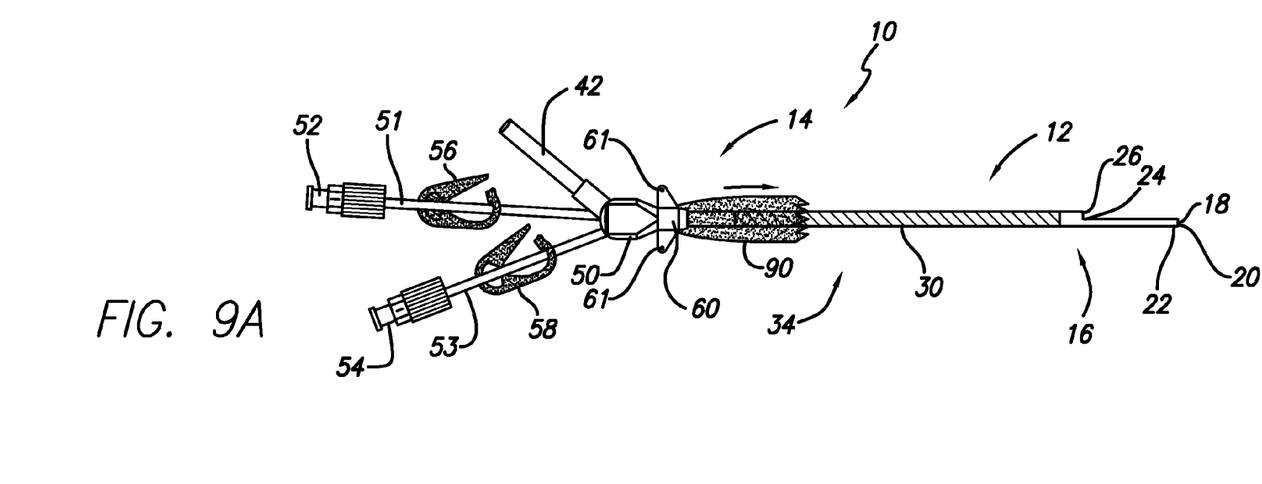
FIG. 9A is a side elevational view of the embodiment shown in FIG. 1A showing occluding material on the shaft.
Figure 9B:
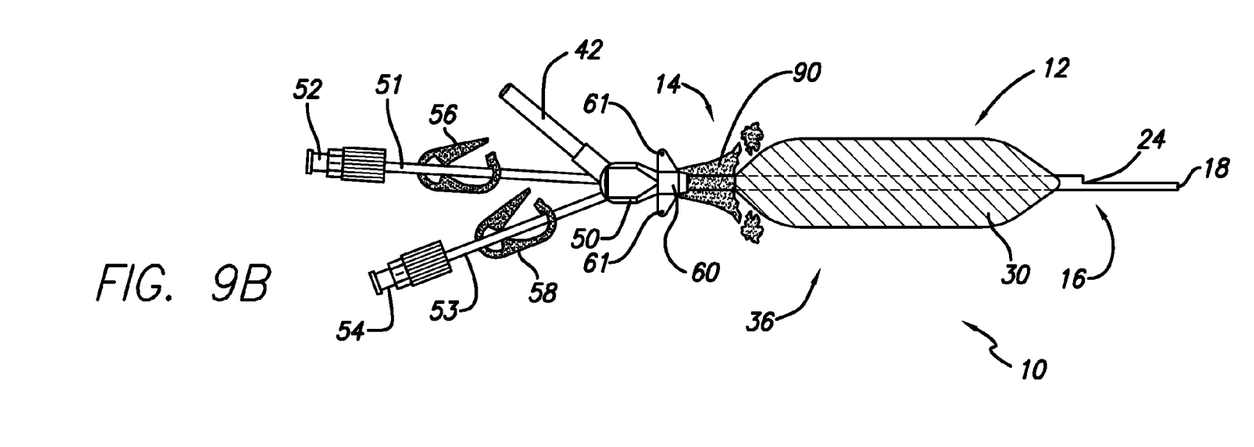
FIG. 9B is a side elevational view of the embodiment shown in FIG. 1B with the occluding material disrupted.

The balloon 30 may be selectively inflated and deflated to disrupt the migration of the occluding material 90 to the distal portion 16 and towards the openings 20, 24. FIG. 9A illustrates the occluding material 90 migrating from the proximal portion 14 of the shaft 12 toward the distal portion 16. FIG. 9B illustrates the disruption of the occluding material 90 with the inflation of the balloon 30. A syringe or other inflation device (not shown) may be connected to the inflation port 42 as described above for inflating and deflating the balloon 30 to disrupt the occluding material 90. The number of inflation/deflation cycles for disrupting the occluding material 90 will depend on several factors, including, but not limited to, the type of device 10, the length of time the device 10 is required to remain indwelling in the patient and rate of migration of the occluding material toward the distal portion 16 of the shaft 12. For example, in one method of treatment, the balloon may be inflated and deflated once while the device 10 is indwelling in the patient. In other methods, multiple inflation/deflation cycles may be used to disrupt the occluding material while the device 10 is indwelling in the patient. The balloon 30 may be inflated during the hemodialysis treatment described above, between hemodialysis treatments or both. In some embodiments, the balloon 30 may remain inflated for a few seconds, or shorter and several inflation/deflation cycles may be used. By way of non-limiting example, the balloon 30 may be inflated 1 second, deflated 5 seconds, inflated 1 second, deflated 5 seconds, inflated 1 second and deflated to disrupt the migration of the occluding material. One skilled in the art will recognize that other inflation/deflation cycles may be used with the present invention.

In some methods of treatment, the distal migration of the occluding material 90 along the shaft 12 toward the distal end 22 may be monitored to determine the number and duration of inflation/deflation cycles for disruption of the occluding material 90. For example, the disrupting material 90 may be viewed using an imaging technique such as MRI or ultrasound where the vessel could be viewed both cranial and caudal to the catheter device 10 to determine the extent of migration of the occluding material 90 and subsequently the extent of disruption.

The amount of inflation of the balloon 30 and the pressure used to inflate the balloon 30 will depend on several factors, including the density of the occluding material 90, the size of the catheter device 10, the size of the vessel in which the device 10 is implanted, and the like. By way of non-limiting example, for a catheter device 10 that is about 14 Fr (about 4.7 mm), the balloon 30 may be inflated about 4 times the size of the catheter device to about 20 mm. In some embodiments, the catheter device may range for about 12 to 16 Fr and the balloon 30 may be expanded to 3-4 times the size of the catheter device 10. Other sizes of catheter devices 10 and ratios of balloon 30 expansion are possible for the present invention. In order to inflate the balloon 30, a specific volume of fluid may be added to provide adequate inflation. By way of non-limiting example, the balloon 30 may be a silicone balloon that may be inflated to 4 times the catheter device 10 that is about 14 Fr using 5 ml of saline to inflate the balloon.

Although the invention herein has been described in connection with a preferred embodiment thereof, it will be appreciated by those skilled in the art that additions, modifications, substitutions, and deletions not specifically described may be made without departing from the spirit and scope of the invention as defined in the appended claims. The scope of the invention is defined by the appended claims, and all devices that come within the meaning of the claims, either literally or by equivalence, are intended to be embraced therein.

The invention claimed is:

1. A method for intraluminal treatment of a patient employing an indwelling catheter device, the method comprising:
    inserting at least a portion of a shaft of a catheter device into a vessel of the patient, the catheter device comprising:
        the shaft including a lumen extending longitudinally therethrough, the lumen having an opening at a distal portion of the shaft; and
        a balloon operably connected to the shaft proximal to the opening;
    providing a treatment through the lumen;
    inflating the balloon; and
    disrupting a migration of occluding material distally on the shaft so as to inhibit the occluding material from occluding the opening in the distal portion of the shaft.

2. The method of claim 1, further comprising the step of providing at least two inflation and deflation cycles.

3. The method of claim 1, comprising the step of inflating the balloon during treatment.

4. The method of claim 1, comprising the step of inflating the balloon before treatment.

5. The method of claim 1, comprising the step of inflating the balloon after treatment.

6. The method of claim 1, further comprising monitoring the occluding material and inflating the balloon.

7. The method of claim 1, further comprising the step of providing a second treatment.

8. The method of claim 1, further comprising the step of coating at least a portion of the indwelling catheter device with an antimicrobial agent.

9. The method of claim 1, wherein the treatment comprises dialysis.

10. A method for intraluminal treatment of a patient employing an indwelling catheter device, the method comprising:
- inserting a distal end of a shaft of a catheter device into a vessel of the patient, the catheter device comprising:
  - a first lumen of the shaft extending longitudinally therethrough to a first opening and a second lumen of the shaft extending longitudinally therethrough to a second opening; and
  - a balloon operably connected to the shaft proximal to the first and second openings, the balloon being connected to an inflation lumen;
- withdrawing a bodily fluid to be treated from the vessel through the second lumen;
- treating the fluid in a treatment instrument;
- infusing the treated fluid through the first lumen into the vessel;
- selectively inflating the balloon; and
- inhibiting occluding material from occluding the first and second openings by disrupting distal migration of the occluding material.

11. The method of claim 10, wherein selectively inflating the balloon comprises providing the balloon in an inflated configuration for a first time segment and providing the balloon in a deflated configuration for a second time segment while the catheter is indwelling.

12. The method of claim 11, wherein the second time segment is greater than the first time segment.

13. The method of claim 11, comprising providing the shaft having the second opening proximal to the first opening.

14. The method of claim 10, comprising providing a hemodialysis treatment.

15. A method for intraluminal treatment of a patient employing an indwelling catheter device, the method comprising:
- inserting a distal end of a shaft of the catheter device into a vessel of the patient, the catheter device comprising:
  - a first lumen extending longitudinally through at least a portion of the shaft to a first opening; and
  - a balloon at least partially surrounding the shaft and operably connected to the shaft proximal to the first opening, the balloon being connected to an inflation lumen;
- securing a proximal portion of the catheter device to the skin of the patient after the distal end has been inserted into the vessel;
- infusing a treatment through the first lumen into the vessel;
- inflating the balloon; and
- inhibiting occluding material from occluding the first opening using the inflation of the balloon to disrupt the distal migration of the occluding material.

16. The method of claim 15, further comprising withdrawing a bodily fluid through a second opening in a second lumen of the catheter device, the second opening positioned distal to the balloon.

17. The method of claim 15, comprising maintaining the balloon within the vessel in a deflated configuration between selective inflations of the balloon.

18. The method of claim 15, comprising inflating and deflating the balloon at least twice while the catheter device is secured to the patient's skin.

19. The method of claim 15, comprising inflating the balloon to at least three times the diameter of the catheter.

20. The method of claim 15, comprising monitoring the occluding material.

* * * * *